(12) United States Patent
Kellerman et al.

(10) Patent No.: US 10,695,065 B1
(45) Date of Patent: Jun. 30, 2020

(54) PERCUTANEOUS ARTERIAL TO VENOUS ANASTOMOSIS CLIP APPLICATION CATHETER SYSTEM AND METHODS

(71) Applicant: Avenu Medical, Inc., San Juan Capistrano, CA (US)

(72) Inventors: Brad M. Kellerman, Escondido, CA (US); Jeffrey E. Hull, Midlothian, VA (US)

(73) Assignee: Avenu Medical, Inc., San Juan Capistrano, CA (US)

( * ) Notice: Subject to any disclaimer, the term of this patent is extended or adjusted under 35 U.S.C. 154(b) by 190 days.

(21) Appl. No.: 16/011,401

(22) Filed: Jun. 18, 2018

Related U.S. Application Data

(62) Division of application No. 14/450,174, filed on Aug. 1, 2014, now Pat. No. 10,070,866.

(60) Provisional application No. 61/861,238, filed on Aug. 1, 2013.

(51) Int. Cl.
*A61B 17/115* (2006.01)
*A61B 18/04* (2006.01)
*A61B 17/11* (2006.01)
*A61B 18/00* (2006.01)

(52) U.S. Cl.
CPC .......... *A61B 17/115* (2013.01); *A61B 18/04* (2013.01); *A61B 2017/1103* (2013.01); *A61B 2017/1107* (2013.01); *A61B 2018/00601* (2013.01)

(58) Field of Classification Search
CPC .................. A61B 17/115; A61B 18/04; A61B 2017/1103; A61B 2017/1107; A61B 2018/00601

USPC ................................................. 600/1; 606/27
See application file for complete search history.

(56) References Cited

U.S. PATENT DOCUMENTS

| | | |
|---|---|---|
| 5,290,278 A | 3/1994 | Anderson |
| 5,330,486 A | 7/1994 | Wilk |
| 5,425,731 A | 6/1995 | Daniel et al. |
| 5,830,222 A | 11/1998 | Makower |
| 5,830,224 A | 11/1998 | Cohn et al. |
| 6,068,637 A | 5/2000 | Popov et al. |
| 6,068,638 A | 5/2000 | Makower |
| 6,071,292 A | 6/2000 | Makower et al. |
| 6,083,223 A | 7/2000 | Baker |
| 6,190,353 B1 | 2/2001 | Makower et al. |

(Continued)

FOREIGN PATENT DOCUMENTS

WO 2011159825 A1 12/2011

*Primary Examiner* — Christopher A Flory
(74) *Attorney, Agent, or Firm* — Stout, Uxa & Buyan, LLP; Donald E. Stout (57) ABSTRACT

A method of creating an anastomosis includes steps of advancing a distal tip of a catheter device through a first blood vessel into a second blood vessel, while simultaneously advancing a proximal base of the device into the first vessel, contacting a wall of the first vessel with a distal blunt surface on the proximal base. A further step is to retract the distal tip so that a proximal blunt base of the distal tip contacts a wall of the second vessel, thereby capturing the two vessel walls between the blunt surfaces of the proximal base and the distal tip. A controlled pressure is applied between the two blunt surfaces to compress and stabilize the captured tissue and approximate the vessel walls. A clip is deployed through the captured tissue to hold the tissue in place during the anastomosis procedure. The anastomosis is created by applying cutting energy to the captured tissue.

28 Claims, 12 Drawing Sheets

(56) References Cited

U.S. PATENT DOCUMENTS

| | | |
|---|---|---|
| 6,235,027 B1 | 5/2001 | Herzon |
| 6,283,983 B1 | 9/2001 | Makower et al. |
| 6,302,875 B1 | 10/2001 | Makower et al. |
| 6,330,884 B1 | 12/2001 | Kim |
| 6,375,615 B1 | 4/2002 | Flaherty et al. |
| 6,379,319 B1 | 4/2002 | Garibotto et al. |
| 6,398,797 B2 | 6/2002 | Bombard et al. |
| 6,409,721 B1 | 6/2002 | Wheelock et al. |
| 6,464,665 B1 | 10/2002 | Heuser |
| 6,533,778 B2 | 3/2003 | Herzon |
| 6,561,998 B1 | 5/2003 | Roth et al. |
| 6,579,311 B1 | 6/2003 | Makower |
| 6,613,081 B2 | 9/2003 | Kim et al. |
| 6,616,675 B1 | 9/2003 | Evard et al. |
| 6,669,709 B1 | 12/2003 | Cohn et al. |
| 6,699,245 B2 | 3/2004 | Dinger et al. |
| 6,709,444 B1 | 3/2004 | Makower |
| 6,726,677 B1 | 4/2004 | Flaherty et al. |
| 6,863,684 B2 | 3/2005 | Kim et al. |
| 6,908,463 B2 | 6/2005 | Treat et al. |
| 6,929,009 B2 | 8/2005 | Makower et al. |
| 7,056,325 B1 | 6/2006 | Makower et al. |
| 7,074,220 B2 | 7/2006 | Hill et al. |
| 7,159,592 B1 | 1/2007 | Makower et al. |
| 7,191,015 B2 | 3/2007 | Lamson et al. |
| 7,316,655 B2 | 1/2008 | Garibotto et al. |
| 7,351,247 B2 | 4/2008 | Kupiecki et al. |
| 7,387,636 B2 | 6/2008 | Cohn et al. |
| 7,588,566 B2 | 9/2009 | Treat et al. |
| 7,729,738 B2 | 6/2010 | Flaherty et al. |
| 7,846,172 B2 | 12/2010 | Makower |
| 8,721,639 B2 | 5/2014 | Mirizzi et al. |
| 8,834,518 B2 | 9/2014 | Faller et al. |
| 9,452,015 B2 | 9/2016 | Kellerman |
| 2002/0072761 A1 | 6/2002 | Abrams |
| 2003/0100920 A1 | 5/2003 | Akin |
| 2004/0073238 A1 | 4/2004 | Makower |
| 2004/0082850 A1 | 4/2004 | Bonner |
| 2004/0204725 A1 | 10/2004 | Bayer |
| 2005/0021085 A1 | 1/2005 | Abrams |
| 2005/0033330 A1 | 2/2005 | Vargas et al. |
| 2005/0038457 A1 | 2/2005 | Vargas et al. |
| 2005/0251167 A1 | 11/2005 | Voegele |
| 2006/0111704 A1 | 5/2006 | Brenneman et al. |
| 2006/0142788 A1 | 6/2006 | Wilson et al. |
| 2006/0189979 A1 | 8/2006 | Esch et al. |
| 2006/0217706 A1 | 9/2006 | Lau et al. |
| 2007/0175963 A1 | 8/2007 | Bilotti |
| 2010/0069934 A1 | 3/2010 | Bombard |
| 2010/0152723 A1 | 6/2010 | Esch et al. |
| 2011/0011916 A1* | 1/2011 | Levine ............... A61B 17/115 227/179.1 |
| 2011/0095067 A1 | 4/2011 | Ohdaira |
| 2011/0251608 A1 | 10/2011 | Timm et al. |
| 2011/0251609 A1 | 10/2011 | Johnson et al. |
| 2011/0306959 A1 | 12/2011 | Kellerman et al. |
| 2011/0306993 A1* | 12/2011 | Hull ............... A61B 17/11 606/151 |
| 2012/0059289 A1 | 3/2012 | Nield |
| 2012/0078246 A1 | 3/2012 | Mirizzi et al. |
| 2012/0302935 A1 | 11/2012 | Miller et al. |
| 2012/0316550 A1 | 12/2012 | Lau et al. |
| 2013/0281998 A1 | 10/2013 | Kellerman et al. |
| 2014/0142561 A1 | 5/2014 | Reu et al. |
| 2015/0025554 A1 | 1/2015 | Suyker |
| 2016/0220245 A1 | 8/2016 | Hausen |
| 2016/0235410 A1 | 8/2016 | Kellerman |
| 2017/0049450 A1 | 2/2017 | Foerster |
| 2017/0071627 A1 | 3/2017 | Kellerman |
| 2017/0086904 A1 | 3/2017 | Reu |
| 2017/0128118 A1 | 5/2017 | Kellerman |

* cited by examiner

PERCUTANEOUS ARTERIAL TO VENOUS ANASTOMOSIS CLIP APPLICATION CATHETER SYSTEM AND METHODS

This application is a divisional application under 35 U.S.C. 120 of U.S. application Ser. No. 14/450,174, entitled Percutaneous Arterial to Venous Anastomosis Clip Application Catheter System and Methods, filed on Aug. 1, 2014, which in turn claims the benefit under 35 U.S.C. 119(e) of the filing date of Provisional U.S. Application Ser. No. 61/861,238, entitled Percutaneous Arterial to Venous Anastomosis Clip Application Catheter System and Methods, filed on Aug. 1, 2013, which applications are each expressly incorporated herein by reference, in their entirety.

BACKGROUND OF THE INVENTION

In the body, various fluids are transported through conduits throughout the organism to perform various essential functions. Blood vessels, arteries, veins, and capillaries carry blood throughout the body, carrying nutrients and waste products to different organs and tissues for processing. Bile ducts carry bile from the liver to the duodenum. Ureters carry urine from the kidneys to the bladder. The intestines carry nutrients and waste products from the mouth to the anus.

In medical practice, there is often a need to connect conduits to one another or to a replacement conduit to treat disease or dysfunction of the existing conduits. The connection created between conduits is called an anastomosis.

In blood vessels, anastomoses are made between veins and arteries, arteries and arteries, or veins and veins. The purpose of these connections is to create either a high flow connection, or fistula, between an artery and a vein, or to carry blood around an obstruction in a replacement conduit, or bypass. The conduit for a bypass is a vein, artery, or prosthetic graft.

An arterio-venous fistula (AVF) is created by connecting an artery to a vein, and to create a leak-free blood flow path between them. This type of connection is used for hemodialysis, to increase exercise tolerance, to keep an artery or vein open, or to provide reliable access for chemotherapy. This is typically done by suturing the vein to the artery in an open surgical procedure. The vein and artery are either attached by an end-to-end anastomosis, end-to-side anastomosis, or a side-to-side anastomosis. The procedure is time consuming, tedious, clinician dependent (open to surgical error), and often results in strictures or clotting of the vein or artery.

It is well know that heat, whether it is Radio Frequency (RF), resistance or laser will attach and weld tissue or vessels upon direct pressure and contact over the targeted weld area. This is often done with jaw-type, compression heat delivery devices. It is also well known that radially expandable devices such as balloons, metal cages and baskets are often coupled with energy in the form of RF, or in the case of balloons, heated saline and used intraluminally to ablate tissue, stop bleeding or create a stricture.

Several catheter-based devices are disclosed herein that are advanced from one vessel into an adjacent vessel (i.e. vein into artery), mechanically couple two vessels together, and then sealing and cutting the anastomosis through the application of heat.

SUMMARY OF THE INVENTION

The present invention eliminates the open procedure described above, reduces operating time, and allows for a consistent and repeatable fistula creation.

More particularly, there is provided an intraluminal anastomotic device which comprises a proximal base having a distal tapered end surface and a distal tip connected to the proximal base and movable relative to the proximal base. The distal tip has a proximal tapered end surface. The distal tapered end surface and the proximal tapered end surface are adapted to contact opposing sides of a tissue portion to create an intraluminal anastomosis. Additionally, a clip housing is disposed on the proximal base.

A plurality of clip applicator guides, comprising clip storage bays, are disposed in spaced relation on the distal tapered end surface of the proximal base. The plurality of clip applicator guides are spaced radially about a circumference of the distal tapered end surface of the proximal base. The clip housing contains a plurality of clips. The device further comprises a clip deployment ring which is movable distally to push a clip through tissue captured between the proximal base and the distal tip.

The clip storage bays are provided for retaining the clips in a predetermined orientation as they are deployed.

In another aspect of the invention, there is disclosed a method of creating an anastomosis, which comprises steps of advancing a distal tip of a catheter device through a first blood vessel and into a second adjacent blood vessel, while simultaneously advancing a proximal base of the device into the first blood vessel, and contacting a wall of the first vessel with a distal blunt surface on the proximal base. A further step is to retract the distal tip so that a proximal blunt base of the distal tip contacts a wall of the second vessel, thereby capturing the two vessel walls between the blunt surfaces of the proximal base and the distal tip. A controlled pressure is applied between the two blunt surfaces to compress and stabilize the captured tissue and approximate the two vessel walls. A clip is then deployed through the captured tissue. The anastomosis is created by applying cutting energy to the captured tissue.

The deploying step includes a step of holding the clip in a clip storage bay to maintain a desired orientation of the clip when it is deployed, and also comprises advancing a clip deployment ring on which the clip is disposed to push the clip into the captured tissue.

The deploying step further includes deploying a plurality of clips into the captured tissue. The plurality of clips may be deployed in stages by first advancing a clip deployment mechanism a first distance into the first vessel and deploying at least one clip into the tissue comprising the first vessel, and then further advancing the clip deployment mechanism a second distance into the second vessel and deploying at least one clip into the tissue comprising the second vessel.

Deployment of the at least one clip into the tissue comprising the second vessel is performed by retracting the clip deployment mechanism. During retracting of the clip deployment mechanism, the method further comprises a step of applying continued pressure on the captured tissue in order to ensure that the vessels do not move apart during the anastomosis procedure.

The invention, together with additional features and advantages thereof, may best be understood by reference to the following description taken in conjunction with the accompanying illustrative drawings.

DESCRIPTION OF THE PREFERRED EMBODIMENT

Referring now more particularly to the drawings, there is shown in FIGS. 1-9 one embodiment of a catheter or intraluminal anastomotic device 1 constructed in accordance with the principles of the present invention. The catheter device 1 tracks over a guidewire which has been placed from one vessel into an adjacent vessel, or any other two anatomical structures.

Figure 1:
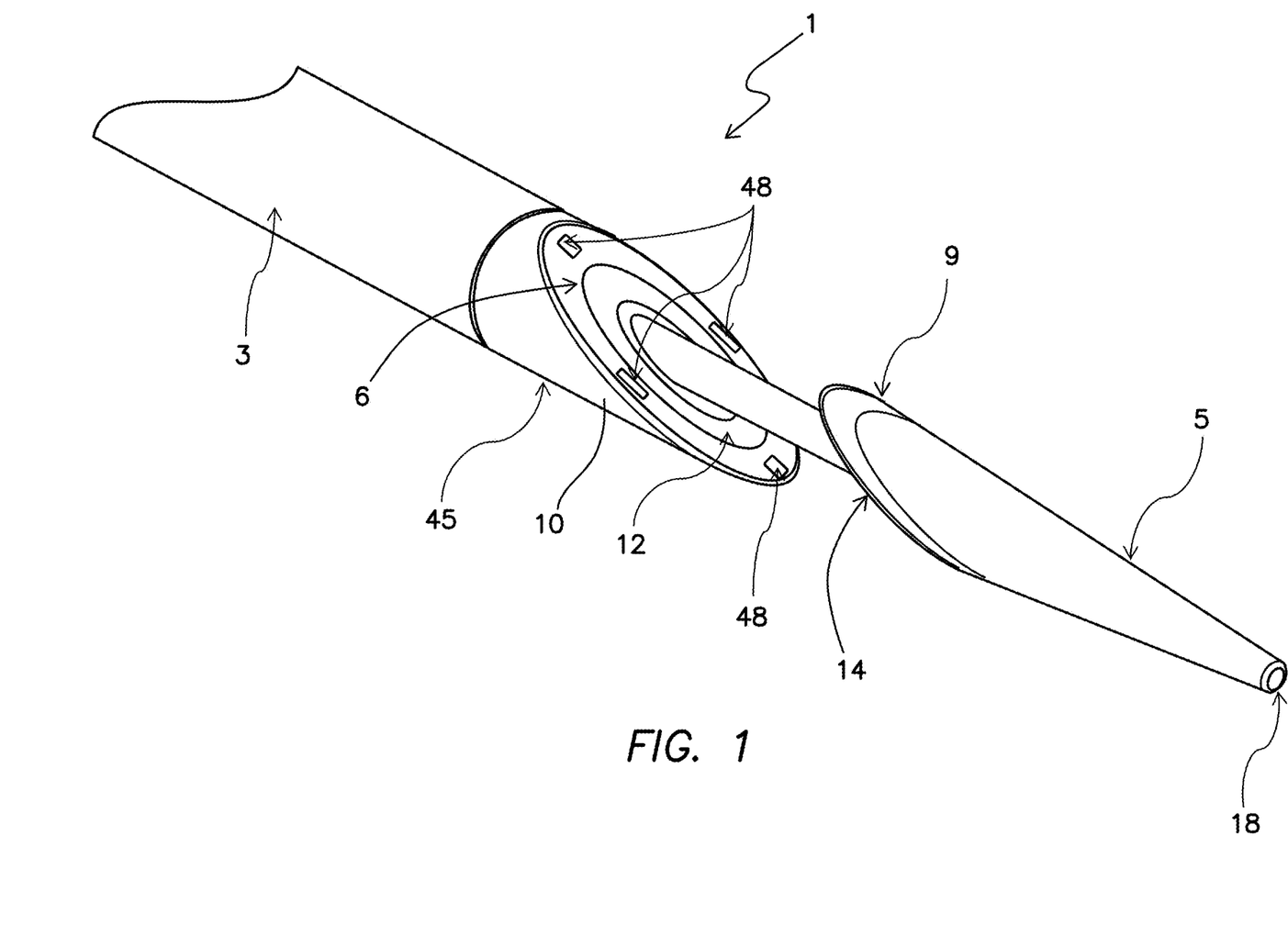
FIG. 1 is an isometric view of one embodiment of the device of the present invention in an extended orientation.
Figure 2:
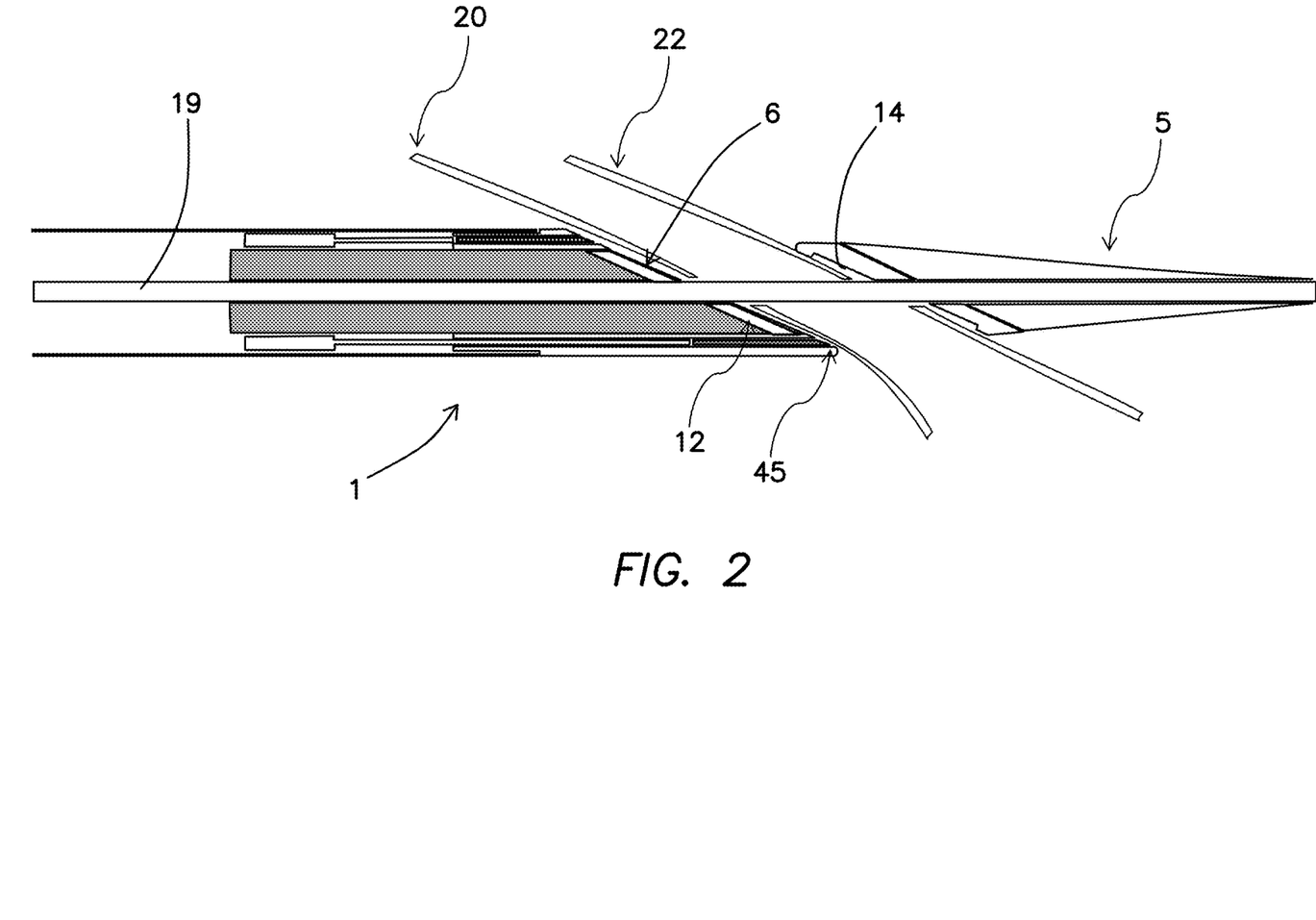
FIG. 2 is a schematic side view of the device of FIG. 1, after a first insertion to a procedural site.

Referring now to FIG. 1, a distal tip 5 of the catheter device 1 has a smooth taper from a 0.014 inch guidewire lumen up to the full diameter, which allows the catheter to advance easily through the vessel walls. Proximal to the distal tip 5, the catheter has a significant reduction in diameter, and then a blunt, oval-shaped tapered proximal surface 6, which is formed on a proximal base 3. The blunt oval-shaped surface 6 is made up of two separate components, namely, a proximal heater 12 and a clip housing 45. The catheter 1 has a guidewire lumen 18, which allows it to track over a guidewire 19 previously placed between a first lumen and a second lumen, as shown in FIG. 2. Clip applicator guides, comprising clip storage bays 48, are spaced radially around the circumference of the heater.

Figure 3:
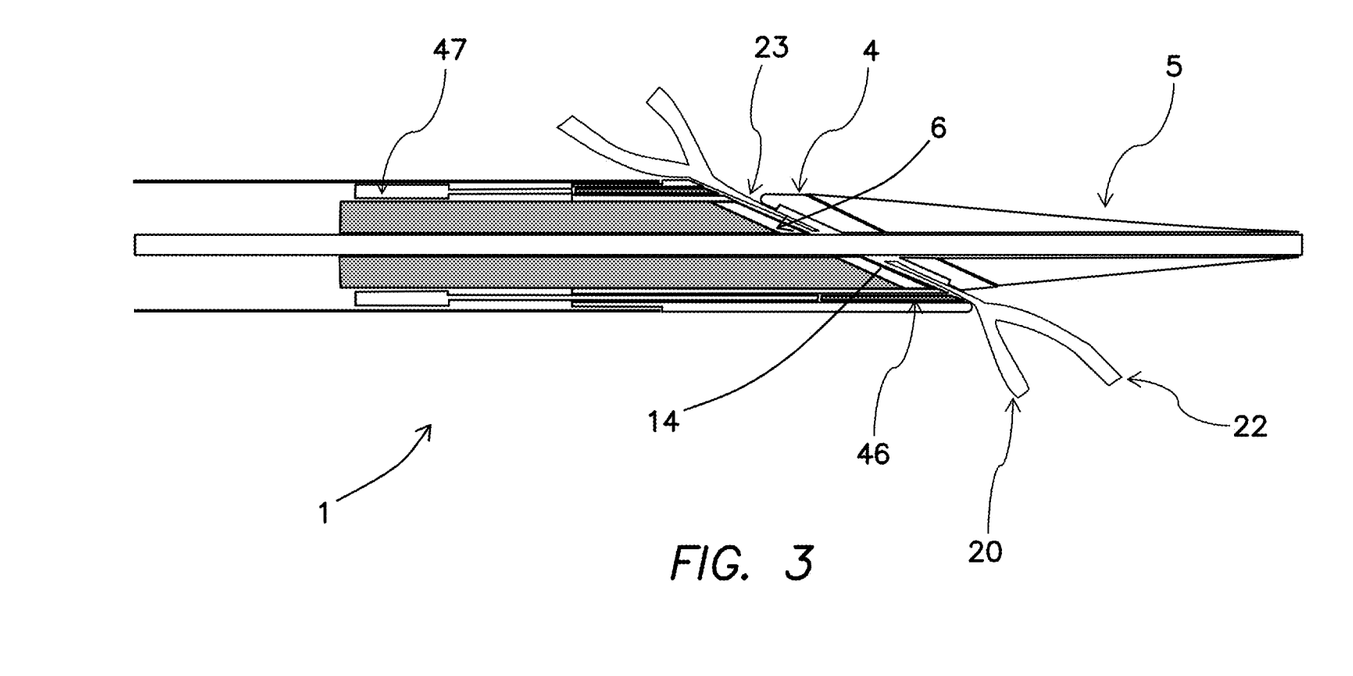
FIG. 3 is a schematic side view, similar to FIG. 2, of the distal end of the device shown in FIG. 2.

As the catheter is tracked over the guidewire 19, the tapered distal tip 5 easily passes from a first vessel 20 into a second vessel 22, so that the device is deployed across the vessels 20, 22 (FIG. 2). After the distal tip passes through the artery, the puncture site recoils down and won't allow the blunt proximal base to pass through the vein into the artery. As the catheter is further advanced, blunt tapered proximal surface 6 comes into contact with the wall of the first vessel 20 and encounters resistance, and cannot perforate through the wall into the second vessel 22 (FIG. 3). The distal tip 5, which has a matching blunt surface 14 on its proximal end 4, is then retracted, capturing and approximating the walls of the two vessels 20, 22 between the two blunt surfaces. A known, controlled pressure (approximately 100 mN/mm$^2$-750 mN/mm$^2$) is applied between the two surfaces to compress and stabilize any tissue that may be between the vessels. The pressure can be controlled either internally in the catheter or by the handle attached to the proximal end of the catheter. There may also be a position monitoring feedback mechanism or sensor which can provide feedback of the amount of tissue captured between the blunt surfaces 6, 14 of the device. The angle between the tip and proximal blunt surfaces creates an anastomosis substantially larger than the diameter of the device.

Figure 4:
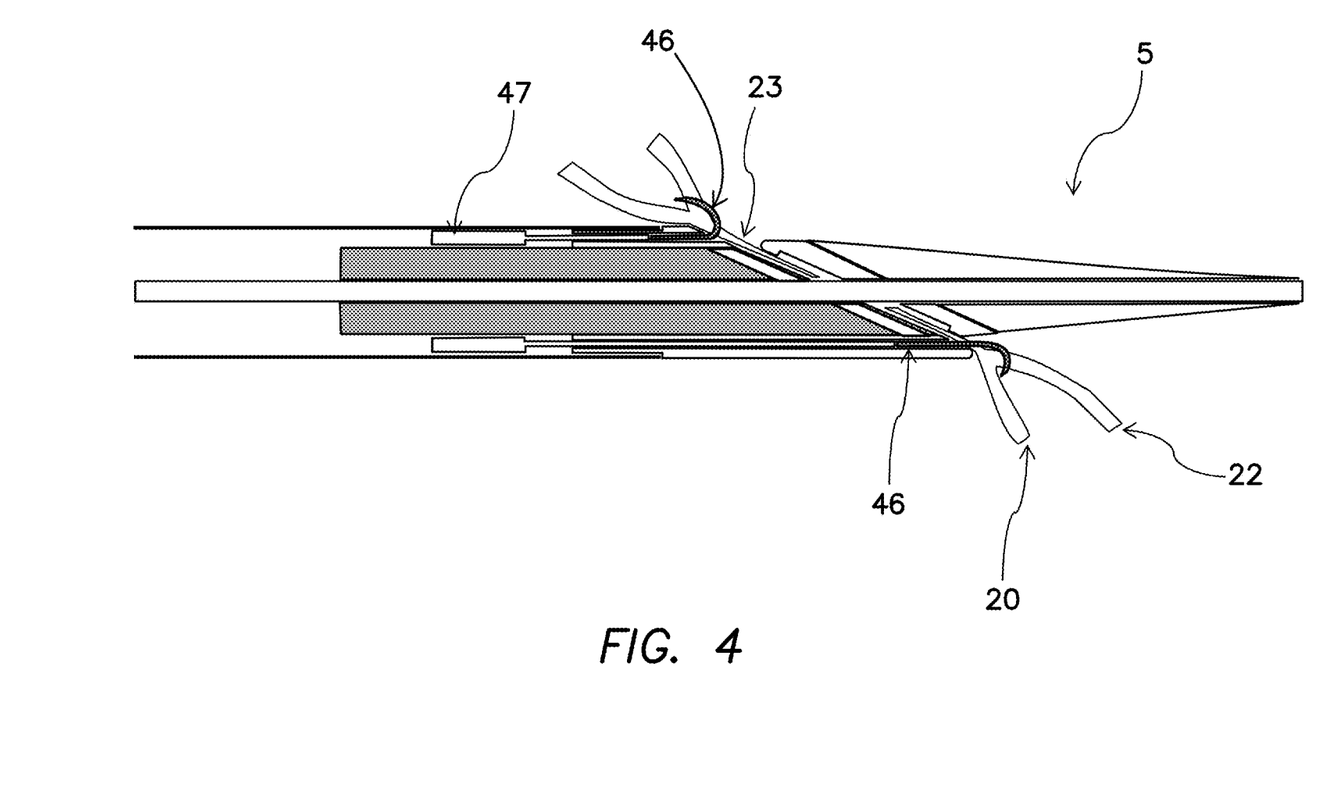
FIG. 4 is a view similar to FIG. 3, wherein tissue is being captured and controlled while clips are deployed.

Referring now to FIG. 4, with the artery and vein walls captured between the two surfaces a clip deployment ring 47 is advanced forward, which pushes a sharp pointed clip through the captured tissue 23. This may be identified as the arterial clip deploy step. Clips 46 can be made of a superelastic material and heat set into an a-like shape. Although Nitinol is currently a preferred material for fabricating the clips 46, other materials may include stainless steel, cobalt chrome, or polymer materials that are known to those skilled in the art. When loaded into the clip housing 45, the clips 46 are held in a straight configuration, but as they are advanced forward, through the wall of the vessel, they begin to return to their α-like shape, clipping the tissue together. In order for the clips to remain in their desired orientation, the cross-section of the clip may be oval, as shown at 41 in FIG. 5, or rectangular (not shown). The curvature of the clip (43a and 43b—FIG. 6b) may be adjusted to determine how much tissue is captured inside the clip (FIG. 6). For instance, it may be desirable that the clip does not puncture through the intima 49 of the second vessel 22. Therefore, the clip does not disturb the flow in the artery and minimizes the neointimal growth (FIG. 6). In this case, the curvature 43b of the clip has such a small radius that it does not penetrate through the adventitia of the adjacent artery before it starts curving back on itself. Contrarily, if strong clipping forces are desired, it is beneficial to pierce deeper into the lumen and capture a larger section of vessel wall, including the adventitia 50, before curving back on itself (FIG. 6a), in which case the curvature 43a of the clip has a large radius primary curve. In one embodiment, the device is shown with four clips, but the number of clips may be modified depending upon the size anastomosis to be created and desired coupling strength.

Figure 5:
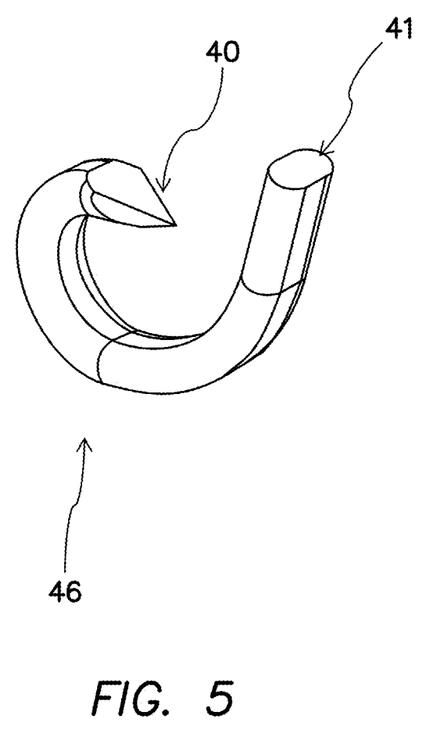
FIG. 5 is an isometric view of a clip constructed in accordance with the principles of the present invention.
Figure 5A:
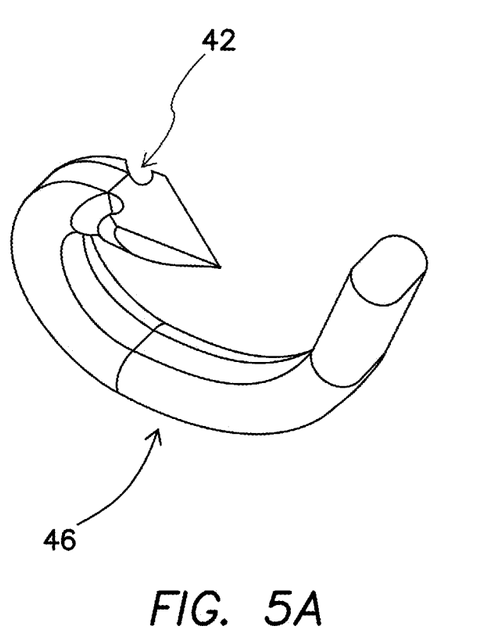
FIG. 5a is an isometric view of a modified clip having a barb.
Figures 6, 6A, 6B:
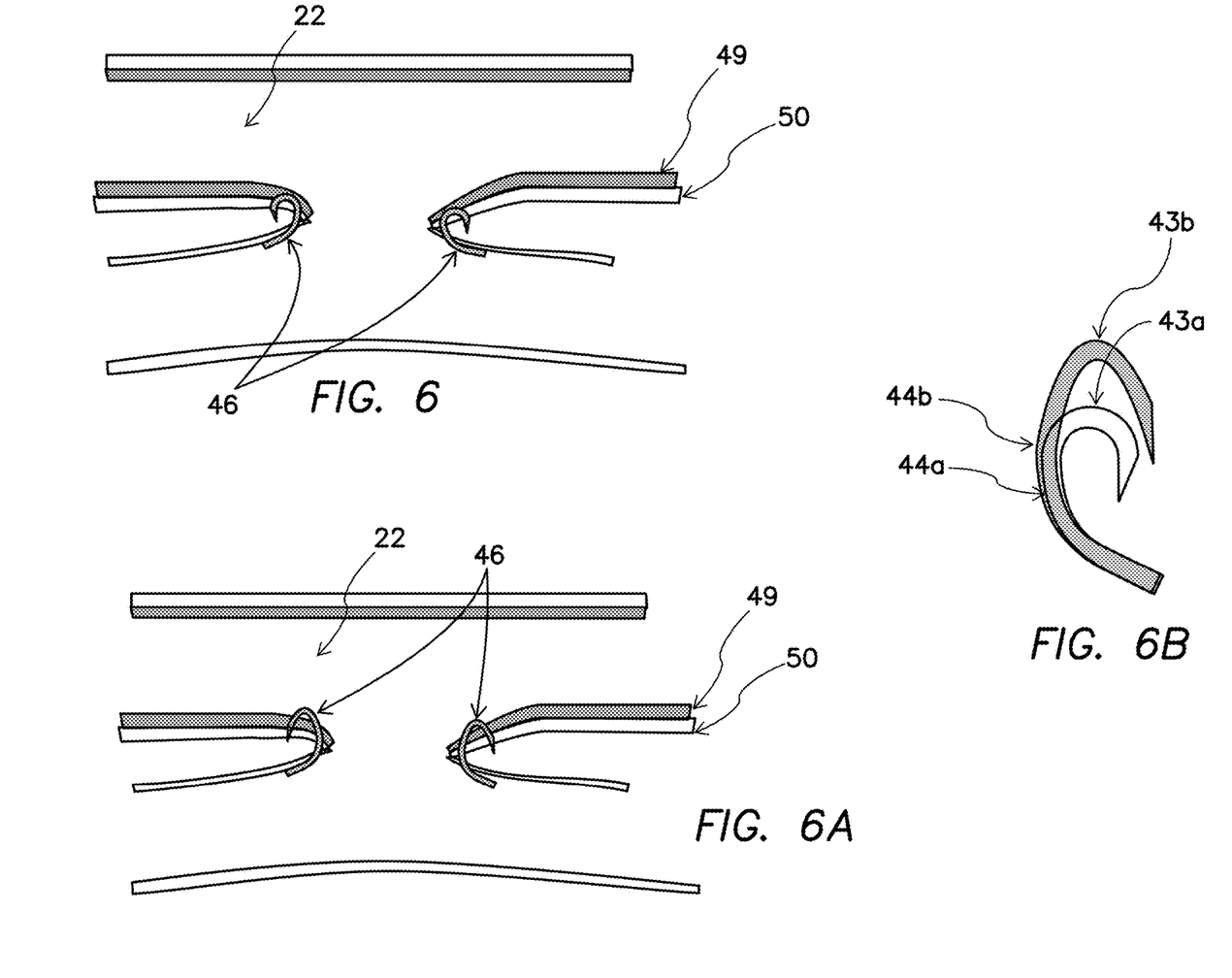
FIG. 6 is a schematic view illustrating the clips capturing only the adventitia of the vessel.
FIG. 6a is a view similar to FIG. 6 wherein the clips puncture through both the adventitia and the intima for greater clipping strength.
FIG. 6b illustrates various curvatures of the inventive clips.

The distal end of the clips 46 are sharpened with a lancet grind profile 40 in order for them to pierce easily through the tissue as they are advanced (FIG. 5). The oval profile 41 of the shape memory clip 46 is such that their orientation is maintained in a clip storage bay 48 and as they are being deployed. It may also be desirable for the clips to have retention barbs 42 to prevent them from migrating once deployed, or as the clip storage bay is being retracted to release them in the first vessel 20, as shown in FIG. 5a.

Figure 7:
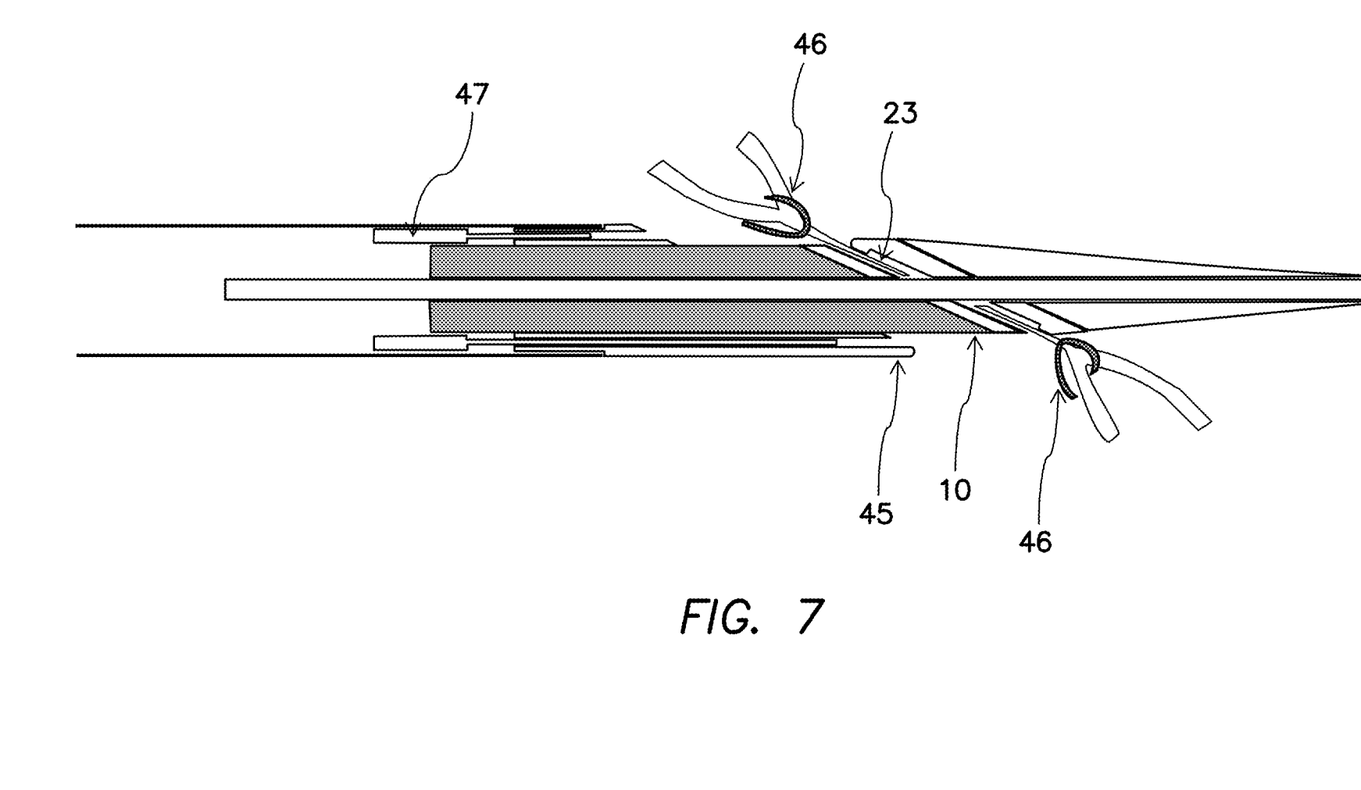
FIG. 7 is a schematic side view illustrating the device of the present invention wherein the clip housing is retracted from the procedural site, leaving the deployed clips behind.
Figure 7A:
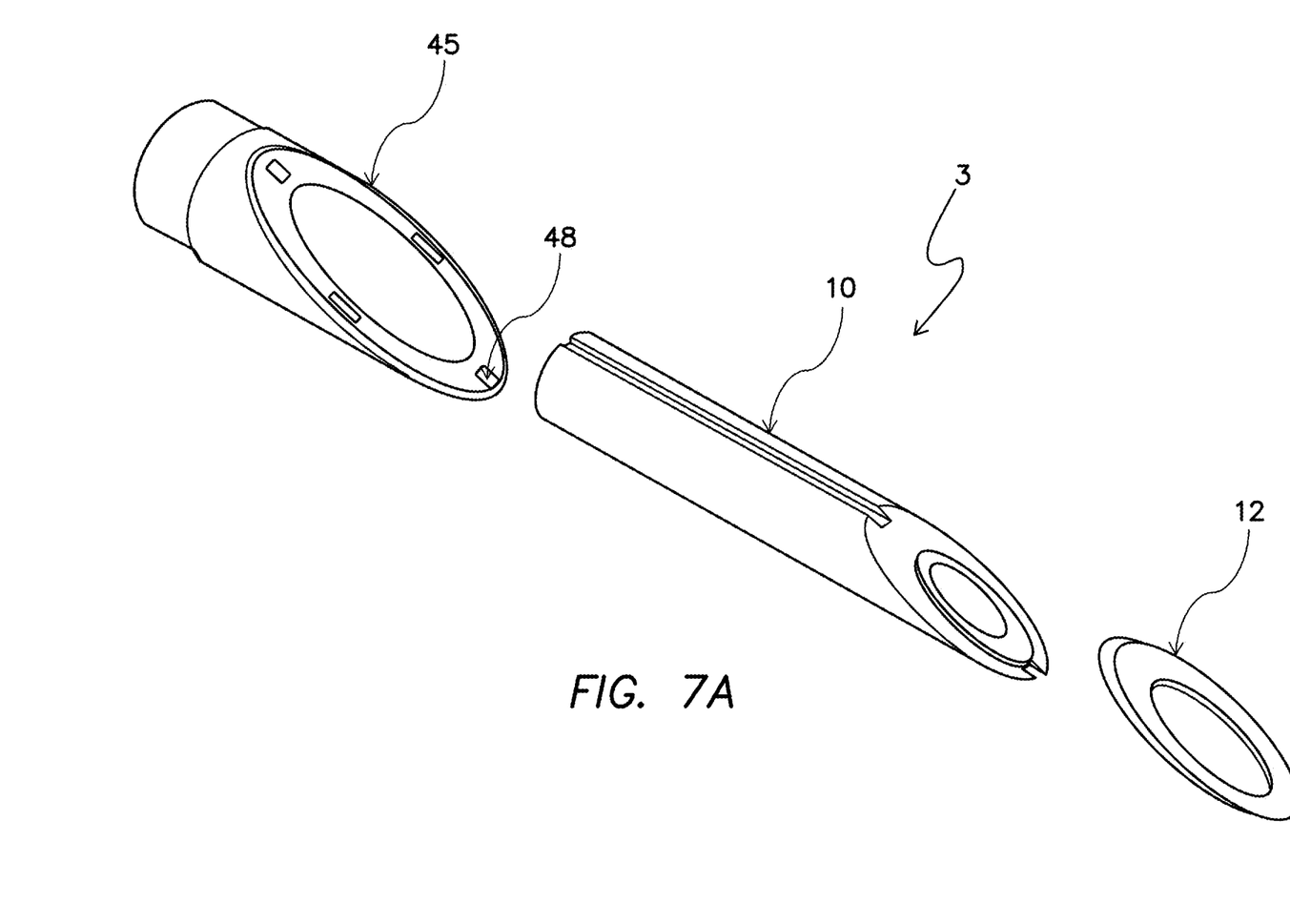
FIG. 7a is an exploded isometric view illustrating the various components of the proximal shaft 3 of the device 1.

After the clips have been advanced into the adjacent second vessel 22, the clips are deployed in the vein by retracting the clip housing 45 (FIG. 7). During retraction of the clip housing 45, the proximal heater 12 on the proximal base 3 maintains pressure on the tissue that is captured between it and the tip. This pressure ensures that the vein cannot move away from the artery, and the clips capture and stabilize the vein to the artery.

Once the clips have been deployed, the anastomosis is created and sized by heating the proximal heater 12. As the proximal heater is heated, the tissue captured between the distal tip 5 and the proximal heater 12 is desiccated and burned away. The tissue immediately surrounding the device is heated to a temperature that is sufficient to denature the proteins within the tissue and create a weld band surrounding the device. The weld band seals the anastomosis and increases its strength. The welding process applicable to this inventive system and method is similar to what has been disclosed in prior commonly assigned U.S. patent application Ser. Nos. 13/161,182, 13/161,356, and 13/763,501, which are herein each expressly incorporated by reference, in their entirety.

Figure 8:
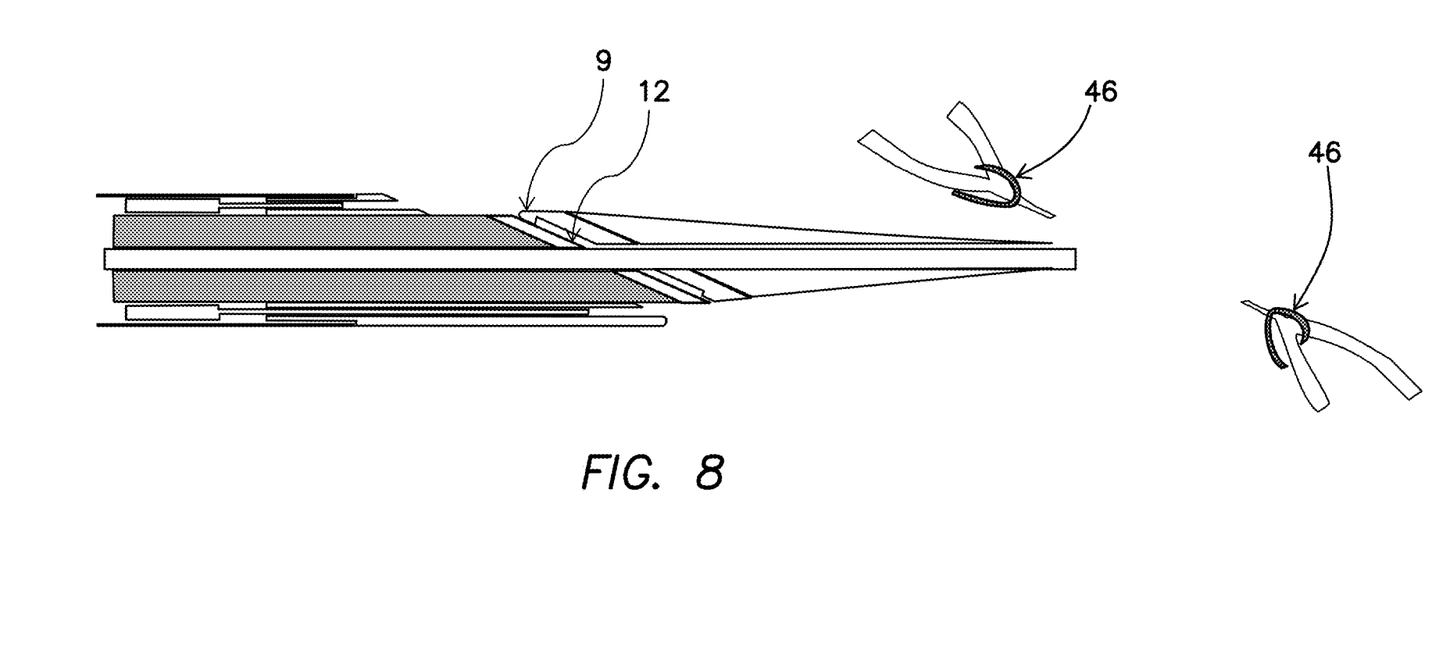
FIG. 8 is a schematic side view wherein the device is being removed from the procedural site, illustrating that the heater profile matches that of the tip so that all material captured under the tip is cut and removed.

Referring now particularly to FIG. 8, the outer profile of a distal heating element 9 aligns with the outer profile of the proximal heater 12 to allow the device to be easily removed once heat has been applied. All of the tissue that has been desiccated remains captured between the distal heating element 9 and the proximal heater 12 to prevent any embolus from being introduced into the vascular system.

Figure 9:
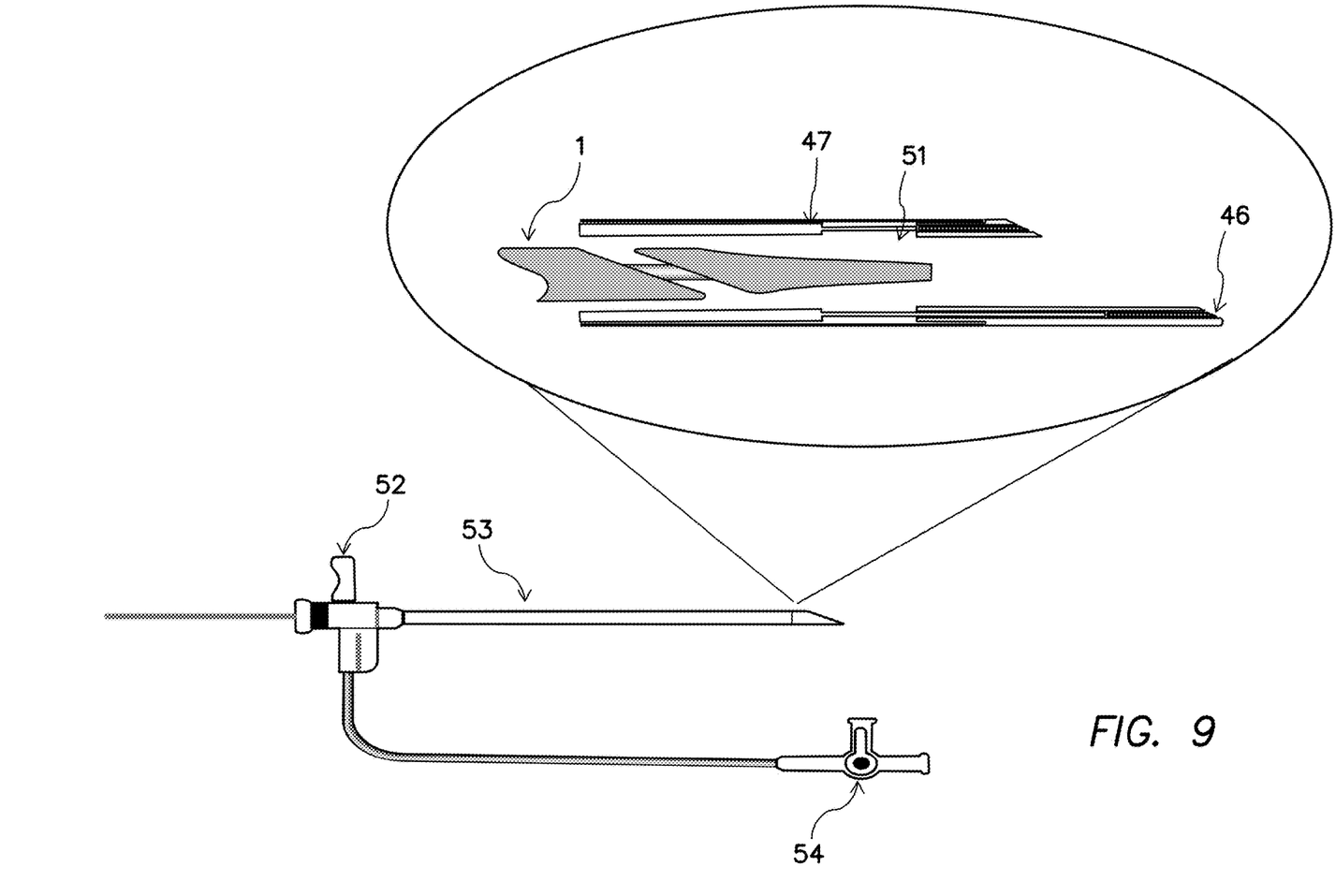
FIG. 9 is a schematic side view of a modified embodiment of the present invention, wherein an introducer sheath is utilized in conjunction with the present invention.
Figure 10:
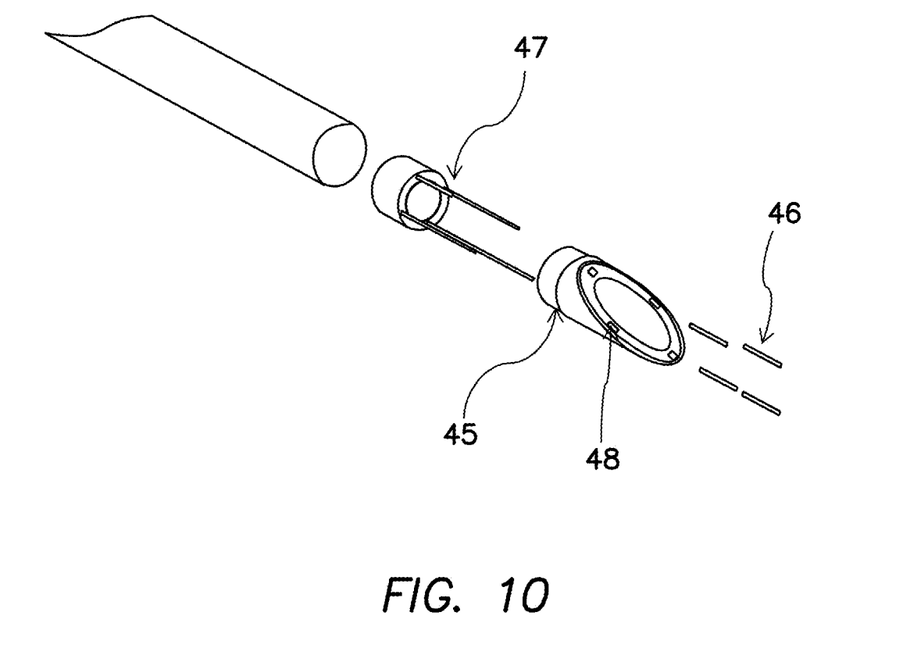
FIG. 10 is an isometric exploded view of the proximal portion of the device of FIG. 9.
Figure 11:
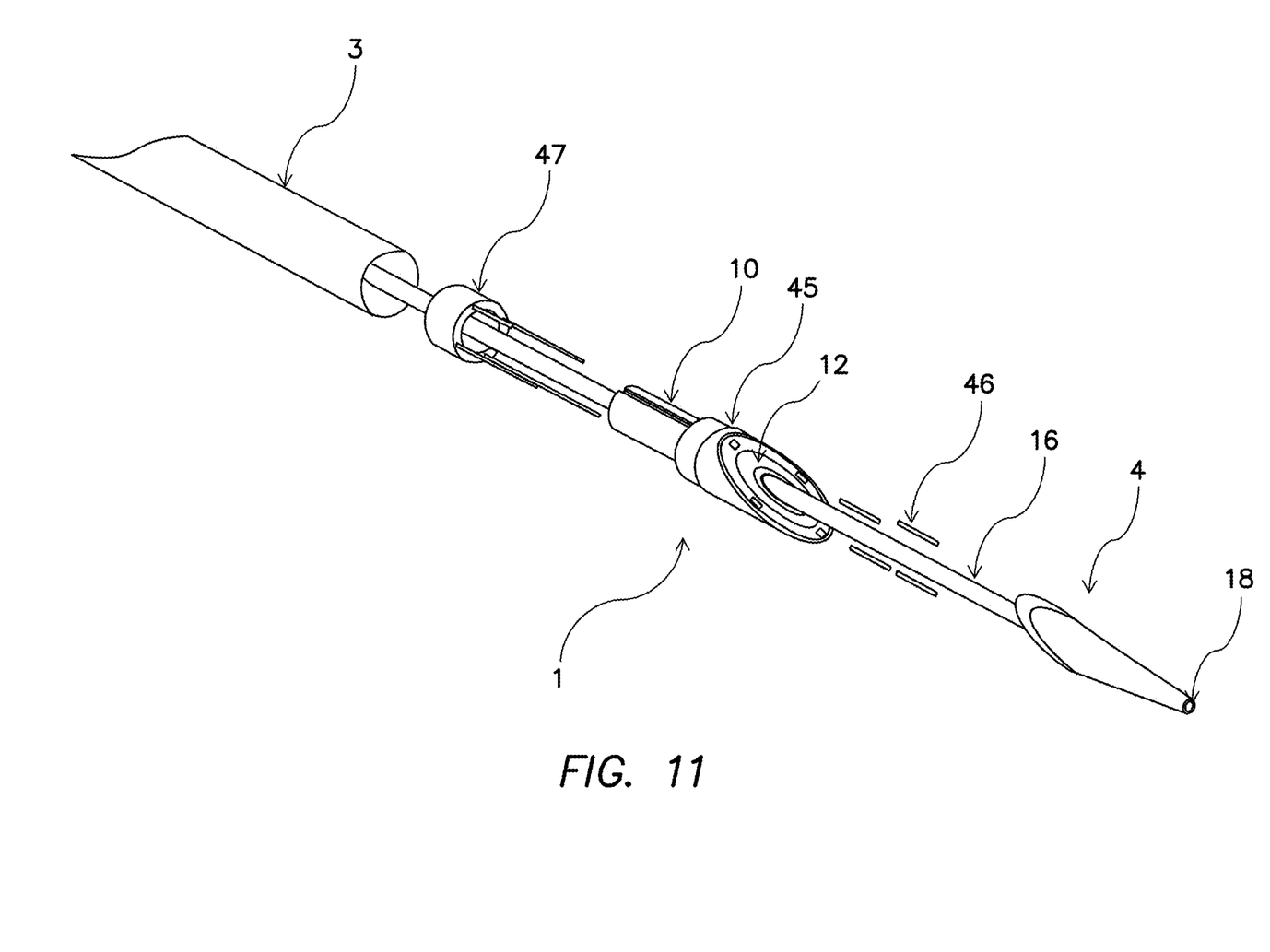
FIG. 11 is an isometric exploded view of the device of FIG. 9.

FIGS. 9-11 illustrate an alternative embodiment of the invention, wherein an introducer sheath is utilized. In this embodiment, like elements are identified by like reference numerals. Introducer sheaths are typically used in surgical procedures where vascular access is needed for multiple different devices. They provide a conduit for devices to be introduced into the vasculature while providing hemostatis. The introducer shown herein also has the capability to dispense clips 46 to secure two anatomical structures together. This introducer sheath works in combination with the intraluminal anastomotic device 1 and procedures previously disclosed in FIGS. 1-8. Once the intraluminal anastomotic device 1 has crossed into the artery and the tip is retracted, the introducer sheath is advanced over the intraluminal anastomotic device shaft until it comes into contact with the vein wall. The tip of the sheath is cut at an angle that matches the intraluminal anastomotic device and mates evenly with the venous wall. With slight forward pressure on the sheath to seat it on the venous wall, the clips are deployed using the same method previously disclosed. After the clips have been deployed, the intraluminal anastomotic device 1 is activated, creating the anastomosis. In the inset of FIG. 9, which is an enlarged view of the distal end of the device, an introducer lumen 51 is disposed within the introducer 53. A hemostasis hub 52 is fluidly connected to a stop cock 54.

Accordingly, although an exemplary embodiment and method according to the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A method of creating an anastomosis, comprising:
   inserting a guide wire through a first blood vessel and into a second adjacent blood vessel;
   advancing simultaneously a distal tip of a catheter device and a proximal base of the catheter device over the guide wire until the distal tip passes through the first blood vessel and into the second adjacent blood vessel and the proximal base of the catheter device within the first blood vessel;
   contacting a first wall of the first blood vessel with a distal blunt surface of the proximal base;
   retracting the distal tip so that a proximal blunt surface of the distal tip contacts a second wall of the second blood vessel, thereby capturing the first wall and the second wall between the distal blunt surface of the proximal base and proximal blunt surface of the distal tip;
   applying a pressure between the distal blunt surface and the proximal blunt surface to compress a tissue between the first wall and the second wall; and
   deploying a clip from within the catheter device into contact with the first wall and the second wall between the first blood vessel and the second blood vessel.

2. The method as recited in claim 1, wherein the deploying step includes holding the clip in a clip storage bay of the catheter device to maintain a desired orientation of the clip when it is deployed.

3. The method as recited in claim 1, wherein the deploying step comprises manipulating a clip deployment actuator within the catheter device to release the clip.

4. The method as recited in claim 1, wherein the deploying step includes deploying a plurality of clips into contact with the first wall and the second wall.

5. The method as recited in claim 4, wherein the deploying step further includes deploying the plurality of clips in stages by first advancing a clip deployment mechanism a first distance into the first blood vessel and deploying at least one clip into the tissue comprising the first blood vessel, and then further advancing the clip deployment mechanism a second distance into the second blood vessel and deploying at least one clip into the tissue comprising the second blood vessel.

6. The method as recited in claim 5, wherein the deploying includes retracting a clip deployment mechanism of the catheter device.

7. The method as recited in claim 6, and further comprising a step of applying continued pressure on the first wall and the second wall during retracting of the clip deployment mechanism to ensure that the first blood vessel and the second blood vessel do not move apart during the anastomosis procedure.

8. The method as recited in claim 1, and further comprising applying cutting energy to the tissue between the first wall and the second wall to produce the anastomosis.

9. The method as recited in claim 1, wherein the clip is stored within a storage bay of the catheter device before the deploying, a shape of the clip corresponding to a shape of the storage bay to maintain the clip in a predetermined orientation within the storage bay.

10. The method as recited in claim 1, wherein the deploying of the clip includes deforming the clip between a first shape configuration and a second shape configuration.

11. The method as recited in claim 1, wherein:
    the proximal base defines a first lumen extending through an entire length of the proximal base;
    the distal tip defines a second lumen extending through the entire length of the distal tip; and
    the advancing simultaneously of the distal tip and the proximal base includes advancing the proximal base over a first portion of the guide wire within a first lumen and a second portion of the guide wire within the second lumen.

12. The method as recited in claim 1, wherein the clip deploying step comprises deploying the clip such that the clip produces a clipping force between the first blood vessel and the second blood vessel.

13. A method of creating an anastomosis, comprising:
    inserting a guide wire through a first blood vessel and into a second blood vessel;
    advancing a catheter device over the guide wire until a distal tip of the catheter device passes through the first blood vessel and into the second blood vessel and a proximal base of the catheter device is within the first blood vessel;

moving the distal tip towards the proximal base to capture a first wall of the first blood vessel and a second wall of the second blood vessel between a distal surface of the proximal base and a proximal surface of the distal tip;

applying a pressure between the distal surface of the proximal base and the proximal surface of the distal tip to compress a tissue between the first wall and the second wall; and deploying a clip from within the catheter device into contact with the first wall and the second wall such that the clip produces a clipping force between the first blood vessel and the second blood vessel.

14. The method as recited in claim 13, wherein:
the clip is stored within a storage bay of the catheter device before the deploying; and
the deploying includes manipulating a clip deployment actuator to release the clip from the storage bay.

15. The method as recited in claim 14, wherein the storage bay is configured to maintain the clip in a predetermined orientation.

16. The method as recited in claim 15, wherein a shape of the clip corresponds to a shape of the storage bay to maintain the clip in the predetermined orientation within the storage bay.

17. The method as recited in claim 13, wherein the clip includes a retention structure configured to maintain the position of the clip relative to at least one of the first wall or the second wall after the deploying step.

18. The method as recited in claim 17, wherein the retention structure comprises a barb.

19. The method as recited in claim 13, wherein the deploying the clip includes deforming the clip between a first shape configuration and a second shape configuration.

20. The method as recited in claim 19, wherein the clip is constructed from a shape memory material.

21. The method as recited in claim 19, wherein the clip is constructed from a polymer.

22. The method as recited in claim 13, further comprising:
applying cutting energy to the tissue between the first wall and the second wall to produce the anastomosis.

23. A method of creating an anastomosis, comprising:
advancing a catheter device into a body until a distal tip of the catheter device passes through a first blood vessel and into a second blood vessel and a proximal base of the catheter device is within the first blood vessel, the catheter device defining a storage bay containing a clip in a predetermined orientation;

moving the distal tip towards the proximal base to capture a first wall of the first blood vessel and a second wall of the second vessel between a distal surface of the proximal base and a proximal surface of the distal tip;

applying a pressure between the distal surface of the proximal base and the proximal surface of the distal tip to compress a tissue between the first wall and the second wall;

releasing a clip from within the storage bay of the catheter device and into contact with the first wall and the second wall such that the clip produces a clipping force between the first blood vessel and the second blood vessel; and removing the catheter device from the body after the releasing.

24. The method as recited in claim 23, wherein a shape of the clip corresponds to a shape of the storage bay to maintain the clip in the predetermined orientation within the storage bay before the releasing.

25. The method as recited in claim 23, wherein the releasing the clip includes manipulating a clip deployment actuator to release the clip from the storage bay.

26. The method as recited in claim 23, wherein the clip is deformed between a first shape configuration and a second shape configuration during the releasing step.

27. The method as recited in claim 23, further comprising:
applying cutting energy to the tissue between the first wall and the second wall to produce the anastomosis.

28. The method as recited in claim 23, wherein the advancing the catheter device is performed percutaneously.

* * * * *